United States Patent
Omi et al.

(10) Patent No.: US 8,610,803 B2
(45) Date of Patent: Dec. 17, 2013

(54) IMAGE PROCESSING APPARATUS FOR ACQUIRING AN IMAGE USING A SPECIFIC IMAGE CAPTURING METHOD AND ACQUIRING AN ANOMALOUS PIXEL USING A DIFFERENT IMAGE CAPTURING METHOD

(75) Inventors: Hiroyuki Omi, Kawasaki (JP); Yohei Minatoya, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 170 days.

(21) Appl. No.: 12/880,497

(22) Filed: Sep. 13, 2010

(65) Prior Publication Data

US 2011/0063469 A1 Mar. 17, 2011

(30) Foreign Application Priority Data

Sep. 16, 2009 (JP) ................. 2009-214696

(51) Int. Cl.
- *H04N 9/64* (2006.01)
- *G01B 15/06* (2006.01)
- *G01N 23/02* (2006.01)
- *G06K 9/00* (2006.01)

(52) U.S. Cl.
USPC .............................. 348/246; 378/58; 382/132

(58) Field of Classification Search
USPC ........ 378/20, 58; 348/241–247; 382/128, 132
See application file for complete search history.

(56) References Cited

U.S. PATENT DOCUMENTS

| | | | |
|---|---|---|---|
| 5,970,115 A * | 10/1999 | Colbeth et al. | 378/62 |
| 6,529,618 B1 * | 3/2003 | Ohara et al. | 382/132 |
| 6,661,456 B1 | 12/2003 | Aufrichtig et al. | |
| 6,763,084 B2 * | 7/2004 | Boehm et al. | 378/62 |
| 7,136,454 B2 * | 11/2006 | Gerndt et al. | 378/98.12 |
| 7,471,765 B2 * | 12/2008 | Jaffray et al. | 378/65 |
| 2003/0095631 A1 * | 5/2003 | Rosner | 378/98.12 |
| 2004/0061785 A1 | 4/2004 | Aufrichtig et al. | |
| 2005/0030412 A1 * | 2/2005 | Nakayama | 348/362 |
| 2005/0259790 A1 | 11/2005 | Gerndt et al. | |
| 2006/0002509 A1 * | 1/2006 | Claus et al. | 378/21 |
| 2007/0019847 A1 * | 1/2007 | Inoue et al. | 382/128 |
| 2008/0297628 A1 * | 12/2008 | Kimura | 348/246 |

FOREIGN PATENT DOCUMENTS

| | | | |
|---|---|---|---|
| JP | 2000-101925 A | 4/2000 |
| JP | 2001-008928 A | 1/2001 |
| JP | 2003-190134 A | 7/2003 |
| JP | 2008-022520 A | 1/2008 |

* cited by examiner

*Primary Examiner* — Kelly L Jerabek (74) *Attorney, Agent, or Firm* — Canon USA Inc. IP Division (57) ABSTRACT

An image processing apparatus includes an image acquisition unit configured to acquire an image captured according to a predetermined image capturing method, an anomalous pixel acquisition unit configured to acquire an anomalous pixel occurring according to an image capturing method different from the predetermined image capturing method, and a display control unit configured to cause the acquired anomalous pixel to be displayed together with the captured image.

8 Claims, 7 Drawing Sheets

IMAGE PROCESSING APPARATUS FOR ACQUIRING AN IMAGE USING A SPECIFIC IMAGE CAPTURING METHOD AND ACQUIRING AN ANOMALOUS PIXEL USING A DIFFERENT IMAGE CAPTURING METHOD

BACKGROUND OF THE INVENTION

1. Field of the Invention

The present invention relates to an image processing apparatus, an image processing system, and an image processing method, for causing positions of anomalous pixels occurring on an image captured by the imaging apparatus to be displayed, and a computer program for executing the image processing method.

2. Description of the Related Art

An image acquired by an imaging apparatus is composed of a plurality of pixels and the image is formed such that the color and density of the image are expressed as a whole by the plurality of pixels. The plurality of pixels may include pixels which are referred to as anomalous pixels. Examples of the anomalous pixel include a defective pixel and a pixel indicating an abnormal value or defective value. The defective pixel indicates an output outside an output range that is preliminary set to a predetermined input due to an abnormality of a circuit or an element in the imaging apparatus.

Since the anomalous pixels adversely affect a quality of the captured image, the anomalous pixels can be corrected according to a method to replace the anomalous pixels by using an average pixel value calculated based on values of the neighboring pixels. Accordingly, an image is provided to a user after the anomalous pixels of the image are corrected. Further, since the anomalous pixels are extracted as the abnormal value in the image, positions of the anomalous pixels change depending on an image capturing method. Japanese Patent Application Laid-Open No. 2000-101925 discusses a technique for correcting the positions of the anomalous pixels which change according to a shutter speed in view of the above described point.

On the other hand, for example, in the medical field, the positions where there were the anomalous pixels need to be confirmed, in order to check if the anomalous pixels are properly changed or not.

Japanese Patent Application Laid-Open No. 2001-8928 discusses such a technique that displays positions of the anomalous pixels which are within a region selected by a user in a radiation image.

There is a situation that an object image is captured using a plurality of image capturing methods sequentially. More specifically, for example, the user captures a high-definition still image of a moving object at an appropriate position and an appropriate timing while observing the object in capturing a moving image of the object. At that time, there is such a demand that a position of the imaging apparatus is adjusted such that the anomalous pixels are not included within the region of the focusing object upon capturing a still image of the object. However, the above-mentioned document has no description about how to display the anomalous pixels of which positions change depending on the image capturing method. Therefore, the above-described demand may not be resolved.

SUMMARY OF THE INVENTION

The present invention is directed to allowing a user to confirm any adverse affect caused by anomalous pixels of an image captured according to an image capturing method different from an image capturing method used in capturing the currently displayed image, thereby prompting the user to perform adjustment.

According to an aspect of the present invention, an image processing apparatus includes an image acquisition unit configured to acquire an image captured according to a predetermined image capturing method, an anomalous pixel acquisition unit configured to acquire a position of an anomalous pixel occurring on an image captured according to an image capturing method different from the predetermined image capturing method, and a display control unit configured to cause the acquired position of the anomalous pixel to be displayed together with the acquired image.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

In the present exemplary embodiment, an anomalous pixel is an abnormal pixel or a defectively output pixel. In other words, the anomalous pixel is a pixel of which pixel value is far off a range of the pixel value of the neighboring pixels. Alternatively, the anomalous pixel is a pixel in which a sensor reads out an abnormality. In the below described exemplary embodiment, the defective pixels, occurring due to the abnormality of an element or a circuit, among the anomalous pixels are exemplified as an example of the anomalous pixel.

In an X-ray imaging system according to a first exemplary embodiment of the present invention, an image captured by a detector 102 is displayed on a display unit 103. The X-ray imaging system functions as an image processing system, which displays a moving image captured by the detector 102 together with the defective pixels occurring on a still image.

Figure 1:
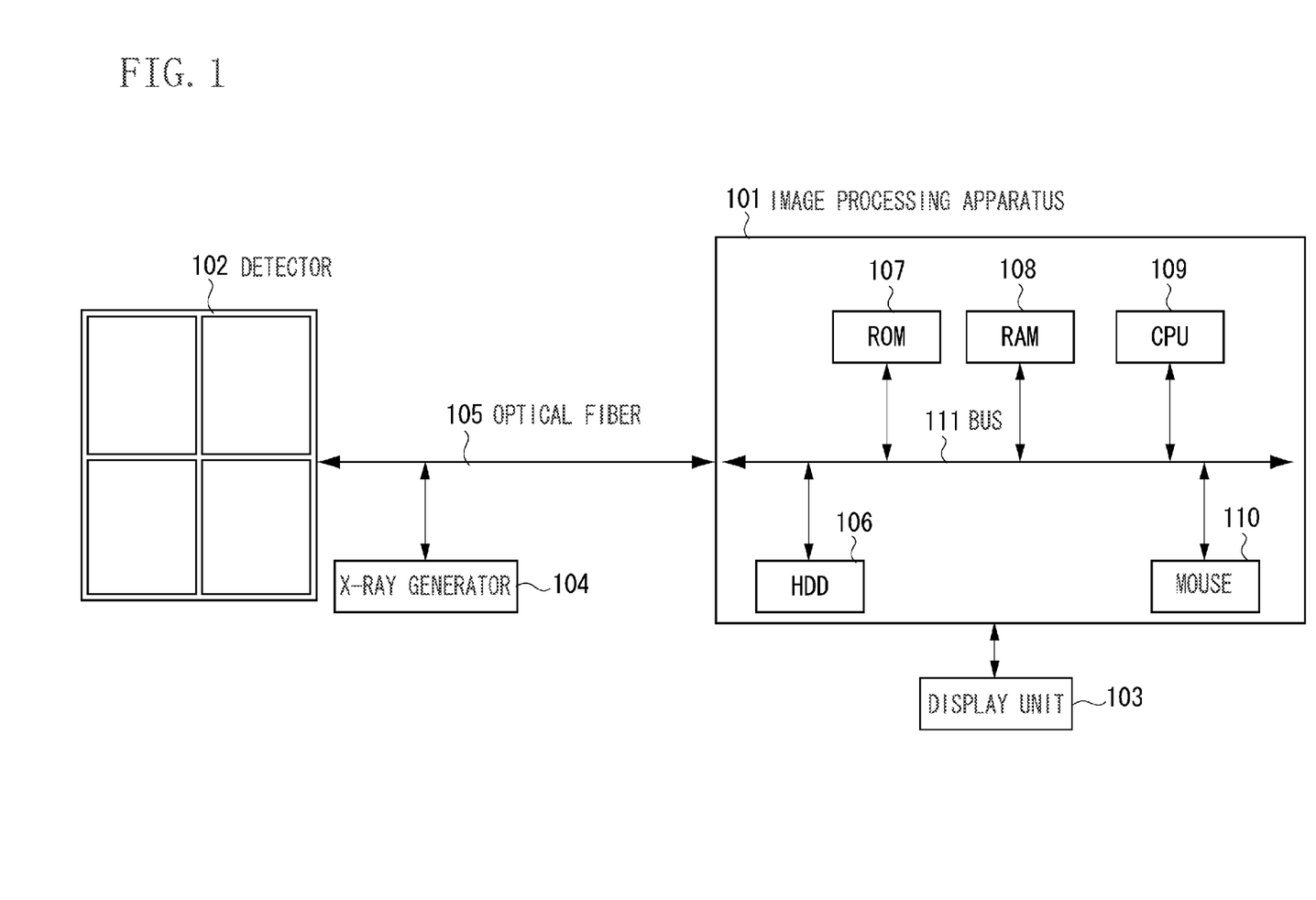
FIG. 1 illustrates a configuration of an X-ray imaging system according to an exemplary embodiment of the present invention.

Now, a configuration of the X-ray imaging system illustrated in FIG. 1 is described below. An X-ray generator 104 irradiates an object with X-rays. Then, the detector 102, which synchronizes with the X-ray generator 104 detects the X-rays. The detector 102 converts thus detected X-rays into an electric charge and stores the electric charge. The detector 102 further reads out the electric charge in the form of an electrical signal to form an object image according to predetermined processing. An image processing apparatus 101 acquires the object image via an optical fiber 105 as a signal line and stores the object image in a storage area of a hard disk drive (HDD) 106. In addition thereto, the image processing apparatus 101 displays the object image on a display unit 103, which is, for example, a liquid crystal display.

The image processing apparatus 101 includes the HDD 106, a read only memory (ROM) 107, a random access memory (RAM) 108, a central processing unit (CPU) 109, and a mouse 110, which are connected to each other through a bus 111. The HDD 106 stores an image acquired from the detector 102 and necessary information, such as positions of defective pixels. The ROM 107 stores a computer program for realizing functions illustrated in FIG. 2, which are described below, and causing the functions to perform processing illustrated in FIG. 3. The computer program is read onto the RAM 108 and executed by the CPU 109. Accordingly, the image processing apparatus 101 cooperates with the computer program to realize the functions illustrated in FIG. 2 and display processing illustrated in FIG. 3.

Figure 2:
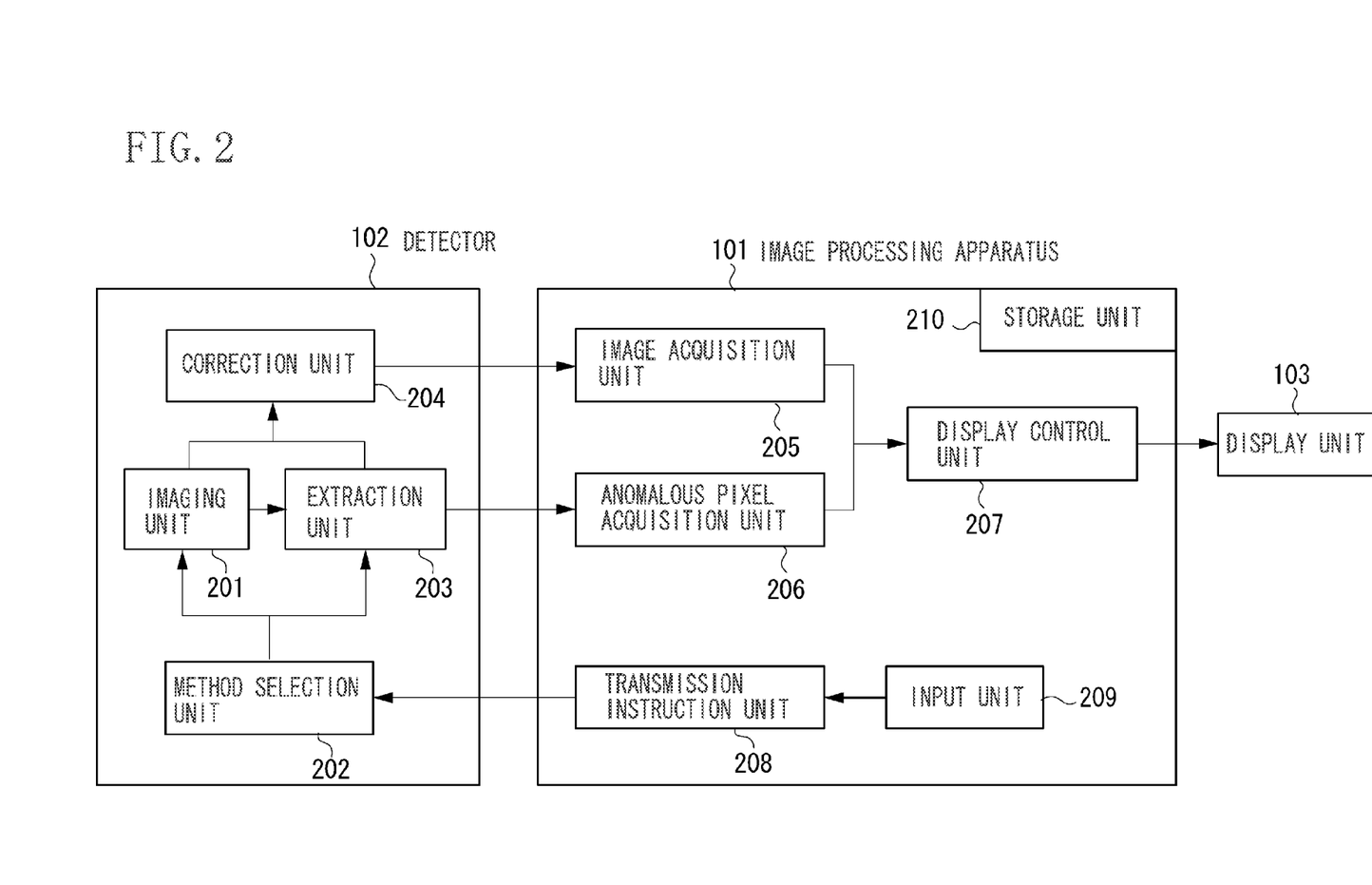
FIG. 2 illustrates a configuration of an image processing apparatus according to an exemplary embodiment of the present invention.

Now, a function realized by the image processing apparatus 101 and the computer program cooperating as described above and a function of the detector 102 are described in detail with reference to FIG. 2. An imaging unit 201 of the detector 102 includes an X-ray sensor and converts X-rays transmitted through the object into an electrical signal. The imaging unit 201 can use a plurality of image capturing methods, e.g., a moving image capturing method, a still image capturing method, and a pixel addition reading method, such as a four-pixel addition reading method. The imaging unit 201 can capture images while changing driving of a circuit of the X-ray sensor according to an instruction of the image capturing method from a method selection unit 202. Then, the imaging unit 201 performs an offset correction or a gain correction to form an image.

An extraction unit 203 is configured to extract defective pixels of the image. The extraction of the defective pixels is to be performed before starting an actual capturing of images. For example, the defective pixels are extracted from a white image, which is obtained by irradiating a sensor with X-rays having uniform intensity. Such an extraction method for defective pixels is used in which an image is divided into predetermined regions and a pixel, of which value is far from an average value of the pixels within the predetermined region by a predetermined times or above, is considered as the defective pixel. This method is identical to an example of the above-described definition of the anomalous pixel and thus may include the anomalous pixels other than the defective pixels. In a case where only the defective pixels are targeted to be extracted, abnormal values other than the values of the defective pixels are removed by using a noise correction method. However, even in a case where the anomalous pixels are extracted in addition to the defective pixels, the adverse affect on the image remains and thus the present invention is still applicable.

Thus extracted defective pixels are stored in a storage unit within the extraction unit 203. Since different defective pixels are obtained according to different image capturing methods, the defective pixels are to be extracted with respect to the white image captured by each of the image capturing methods. A correction unit 204 is configured to correct defective pixels of the image by using the preliminary extracted defective pixels in order to acquire a corrected image. The correction of the defective pixels is performed according to a method in which, for example, a pixel value of each of the defective pixels is substituted with an average value of four neighboring pixels.

The image acquisition unit 205 of the image processing apparatus 101 acquires the corrected image from the detector 102 after the defective pixels of the image are corrected. The image acquisition unit 205 acquires an image from the detector 102 after the image is captured in the case of a still image, whereas the image acquisition unit 205 acquires an image in real time from the detector 102 while a moving image is captured in the case of a moving image. Accordingly, images can be confirmed during image capturing. Thus acquired images are stored in the HDD 106 of the image processing apparatus 101.

An anomalous pixel acquisition unit 206 acquires positions of the defective pixels extracted in the detector 102 together with information as to the image capturing method thereof. The information as to the image capturing method is necessary because the positions of the defective pixels change depending on the image capturing methods. Position information of the defective pixels means data indicating a position of each of the defective pixels in the entire image. For example, the data is bitmap data in which each of defective pixels is indicated by 1 and each of normal pixels is indicated by 0 (hereinafter referred to as a "defective pixel map"). The defective pixel map is stored in the HDD 106.

A display control unit 207 generates display image data, i.e., image data for displaying the defective pixel map obtained by the anomalous pixel acquisition unit 206 together with the image acquired by the image acquisition unit 205. Examples of the display format include a display format that the defective pixels are overlapped on the image and a display format that the defective pixels are displayed separately from the image. In a case where the defective pixels are displayed so as to be overlapped on the image, such display data is to be generated that the positions of the defective pixels are provided with circle marks or cross marks, colored or blinked with reference to the defective pixel map. The data is generated such that, in a case where data of the pixel is 1 with reference to the defective pixel map, the pixel is highlighted in a manner as described above and the same is done for all the other pixels, whereas, in a case where the data of the pixel is 0 with reference to the defective pixel map, the moving image data is displayed as it is without specifically highlighting the pixel. This data is displayed on the display unit 103 so that the below described image display is realized.

A transmission instruction unit 208 is configured to issue an instruction to the detector 102 as to an image of which image capturing method is to be transmitted to the image processing apparatus 101 and an instruction as to a defective pixel map occurring according to which image capturing method is to be transmitted. For example, in a case where the transmission instruction unit 208 issues an instruction for transmitting a moving image and an instruction for transmitting the defective pixels appearing on a still image, the method selection unit 202 of the detector 102 receives the instructions. The imaging unit 201 captures a moving image and transmits the moving image to the image acquisition unit 205 in real time. The extraction unit 203 reads out the defective pixels of the still image from the storage unit and transmits the defective pixels to the anomalous pixel acquisition unit 206. An input unit 209, including, e.g., the mouse 110 or the like, transfers an input by the user to the transmission instruction unit 202.

The storage unit 210 stores the image acquired by the image acquisition unit 205 from the detector 102 and the defective pixel map obtained by the anomalous pixel acquisition unit 206. For example, in a case where the moving image of the object is displayed while capturing the moving image of the object and the moving image is not recorded, each of frame images of the moving image is only read onto the RAM 108 and displayed on the display unit 103 but is not necessarily stored in the storage unit 210.

Figure 3:
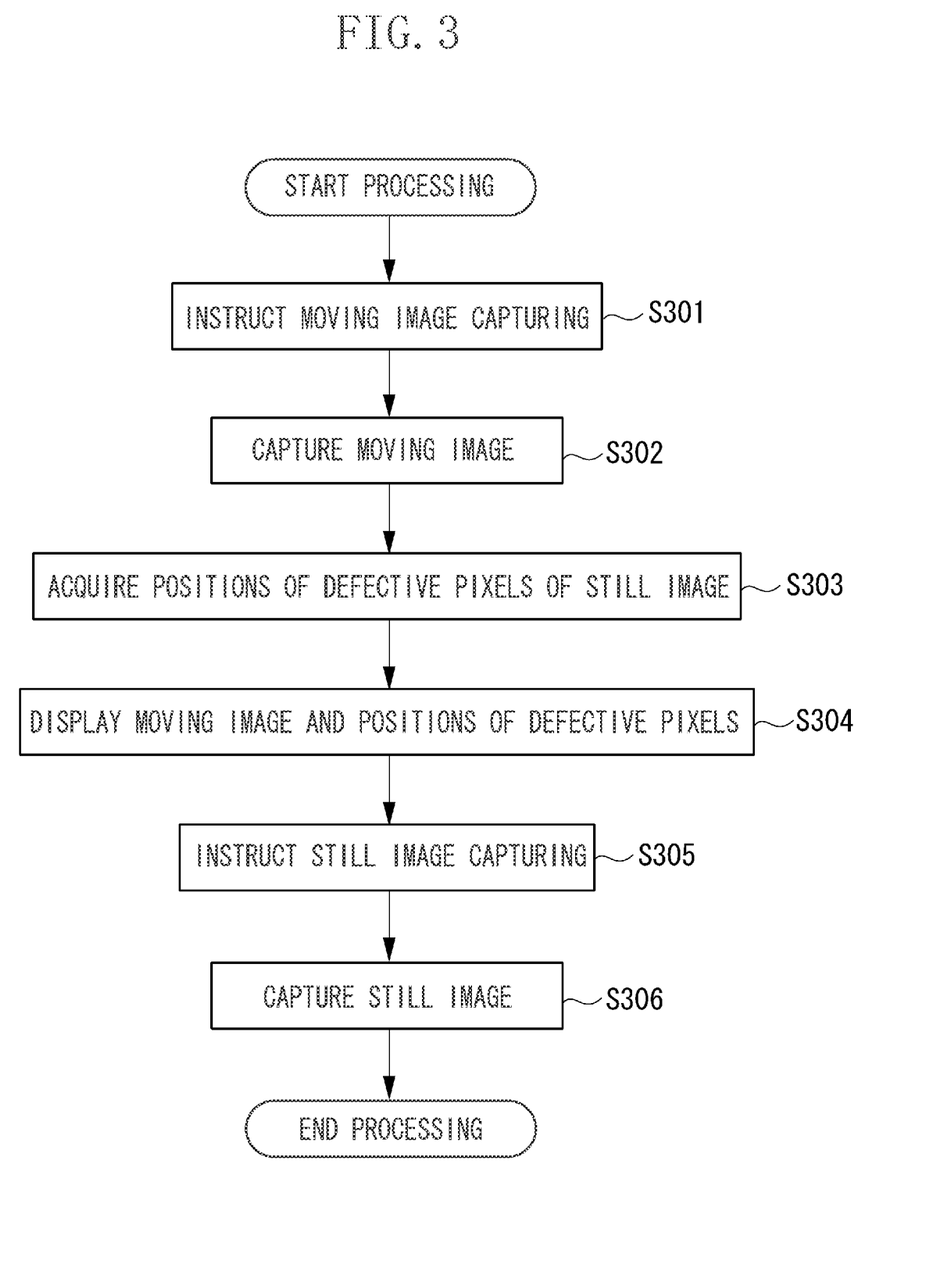
FIG. 3 is a flow chart illustrating a flow of processing according to a first exemplary embodiment of the present invention.

A flow of processing executed by the X-ray imaging system which has the above described configuration is described below with reference to FIG. 3. This processing is performed such that each of hardware resources of the image processing apparatus 101 cooperates with a program, which is read and executed by the CPU 109. However, for the sake of the convenience in a description of this processing, a functional block of FIG. 2 which is realized by the cooperation of the hardware with the software is mainly described below.

In step S301, the transmission instruction unit 208 issues an instruction for capturing a moving image according to an input by the user. The method selection unit 202 of the detector 102 instructs the imaging unit 201 to capture a moving image according to the instruction. The correction unit 204 corrects defective pixels of the moving image and transmits the corrected moving image to the image processing apparatus 101 in real time. Instep S302, the image acquisition unit 205 then acquires the moving image. In step S303, as the moving image is acquired by the image acquisition unit 205, the anomalous pixel acquisition unit 206 acquires the defective pixels of the still image. The transmission instruction unit 208 issues an instruction for transmitting the defective pixels of the still image. The extraction unit 203 of the detector 102 reads out the defective pixel map of the still image from the storage unit. The anomalous pixel acquisition unit 206 acquires the defective pixel map. The anomalous pixel acquisition unit 206 may acquire the defective pixel map in response to an input by the user, concurrently with capturing of the moving image, or according to display of the moving image.

Then, the display control unit 207 generates image data for displaying the defective pixel map of the still image in superimposition on the moving image based on the acquired moving image and the acquired defective pixel map of the still image. This data generation processing may be performed at the same time the moving image and the defective pixel information are acquired or by generating image data for preliminary displaying the moving image and displaying the defective pixels on the moving image. In step S304, the display control unit 207 transmits the image data to the display unit 103 to display the image data. An example of this display screen is described below. With the display of the image data, the user can be notified at which positions the defective pixels appear in the next still image while the user is capturing the moving image and confirming the object image in the moving image. The user can confirm how many defective pixels appear in the region the user desires to pay attention as well as can know to what degree the user may adjust the position of the sensor or the position of the object. Specifically, in a radiation imaging apparatus, such a capturing technique is established that a high-definition still image is captured at an appropriate position or at a good timing while the user is capturing the moving image. The technique is suitably applicable in such case.

In step S305, the transmission instruction unit 208 issues an instruction for capturing the still image in response to an input by the user. In step S306, in accordance with this instruction, the detector 102 executes the still image capturing and the image acquisition unit 205 acquires the resulting image to cause the display unit 103 to display the image via the display control unit 207. Accordingly, an appropriate still image capturing can be realized.

Figure 4A:
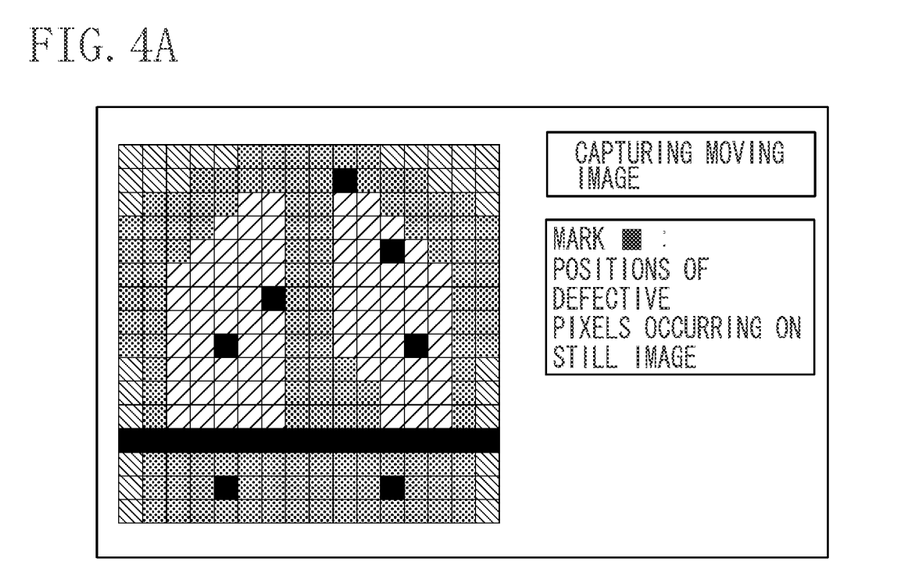
FIGS. 4A and 4B each illustrate a display example according to the first exemplary embodiment.
Figure 4B:
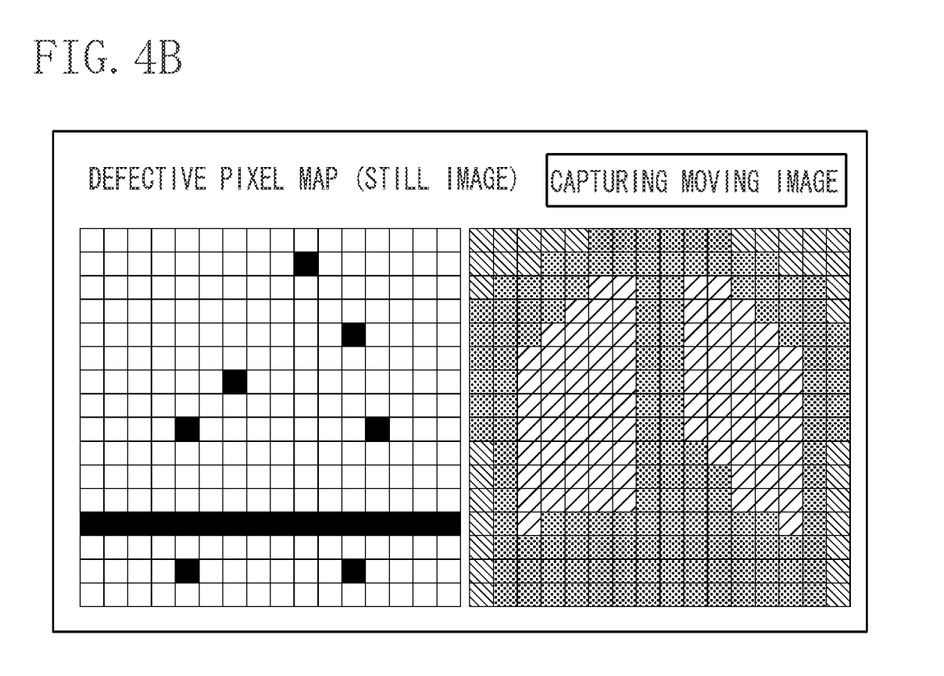

FIGS. 4A and 4B each illustrate an example of a displayed screen realized by the processing in step S304. In the example of screen display illustrated in FIG. 4A, the moving image of the object is displayed on the left side of the screen as well as the positions of the defective pixels in the still image are filled in black color. Alternatively, the positions of the defective pixels in the still image may be colored for the sake of easy discrimination. Information as to the above-described display content is displayed at the right side of the screen. According to this displayed screen, the user can be notified which positions the defective pixels appear in the next still image while the user is capturing the moving image and confirming the object image. In the example of the displayed screen illustrated in FIG. 4B, the defective pixel map is displayed on the left field of the screen as well as the moving image during image capturing is displayed on the right field of the screen. The size of the displayed defective pixel map may set so as to correspond to the size of the moving image. In this case, easy understanding of a correspondence of the sizes between the defective pixel map and the moving image can be provided to the user.

Figure 5:
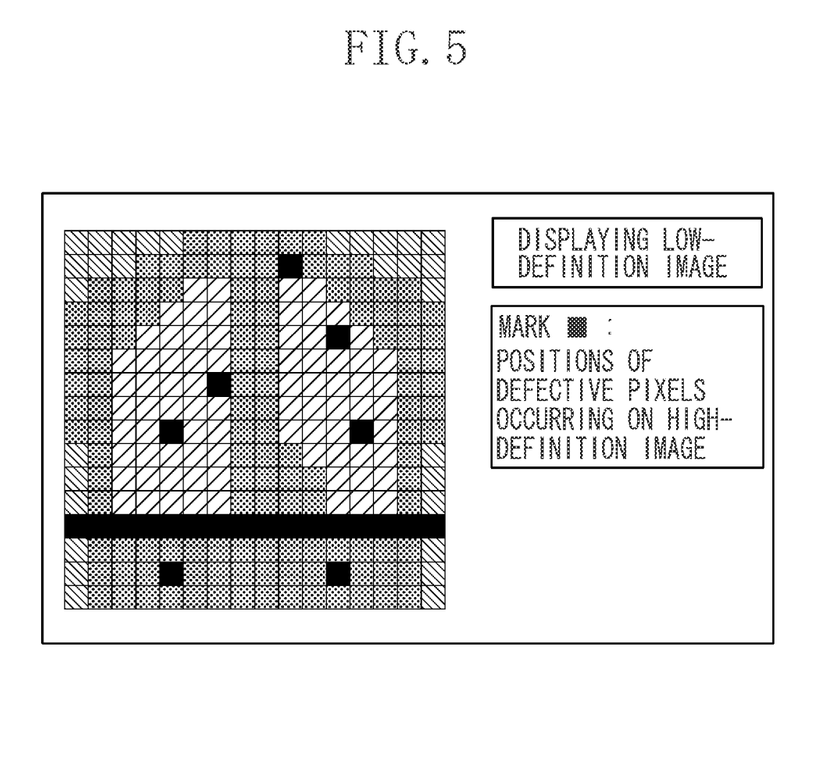
FIG. 5 illustrates another display example according to the first exemplary embodiment.

FIG. 5 illustrates an example of another displayed screen. In FIG. 5, a low-definition image is displayed as well as the positions of the defective pixels occurring in the high-definition image are displayed thereon. The low-definition image can be acquired by the imaging unit 201 according to, for example, a four-pixel addition reading. An instruction for transmitting the image acquired according to the image capturing method in which an image is captured according to the four-pixel addition reading and the defective pixel map obtained according to the image capturing method in which an image is captured without adding any pixels is issued to the detector 102. The image and the defective pixel map are then overlapped to each other and displayed, thereby realizing the displayed screen illustrated in FIG. 5. According to this displayed screen, in a capturing technique that the high-definition image is captured after capturing a low-definition image, the positions of the defective pixels occurring on the high-definition image can be displayed in the low-definition image.

Figure 6:
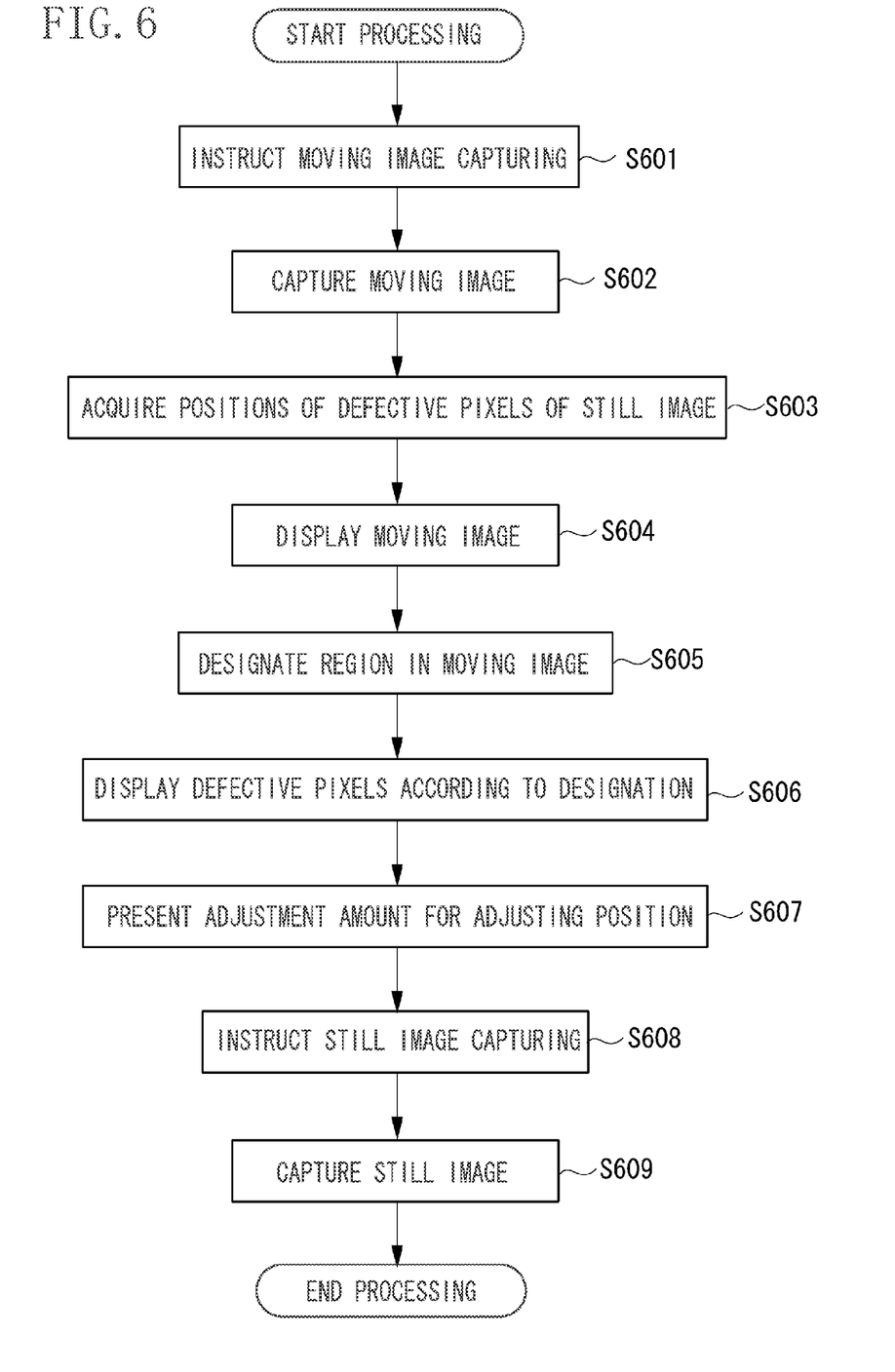
FIG. 6 is a flow chart illustrating a flow of processing according to a second exemplary embodiment of the present invention.
Figure 7A:
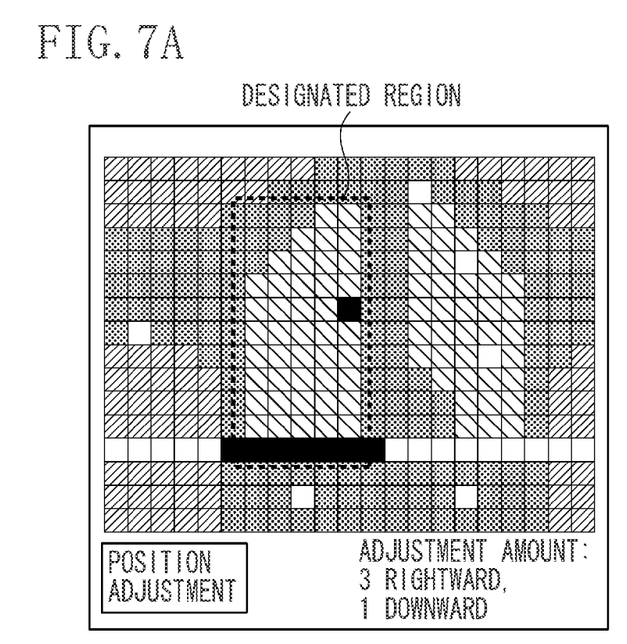
FIGS. 7A through 7C schematically illustrate display examples and a position adjustment method according to the second exemplary embodiment.
Figure 7B:
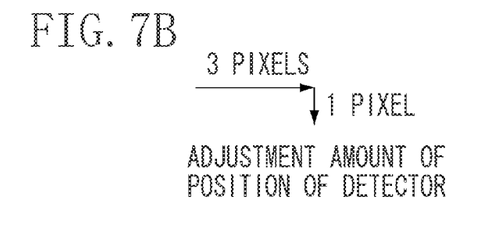
Figure 7C:
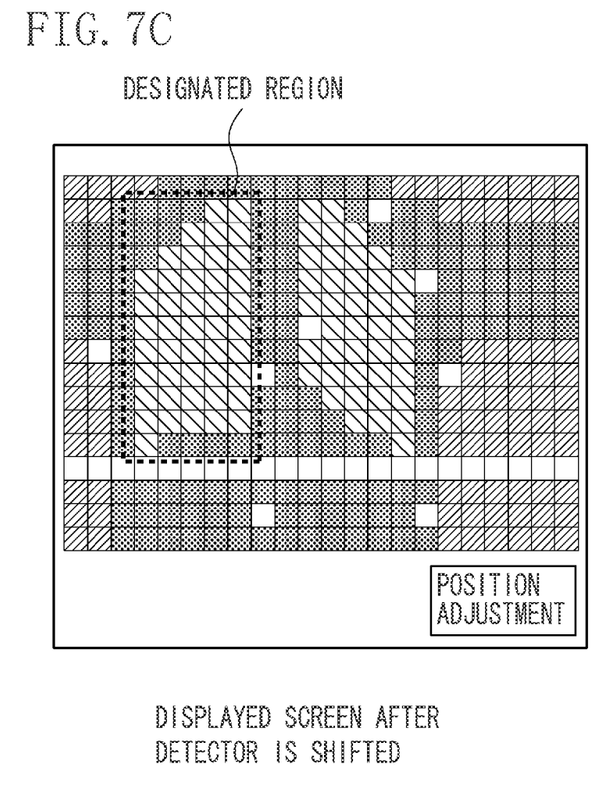

A second exemplary embodiment of the present invention is described below with reference to FIGS. 6 and 7A through 7C. In the present exemplary embodiment, a region on the object image is designated according to an input by the user and different display formats are used in displaying the defective pixels within the designated region and in displaying the defective pixels within regions other than the designated region. Further, in the present exemplary embodiment, in order to adjust the position of the detector 102 in such a manner that the number of defective pixels within the region becomes less as much as possible, an appropriate adjustment amount is provided. FIG. 6 is a flow chart illustrating a flow of processing according to the present exemplary embodiment. FIGS. 7A through 7C schematically illustrate processing according to the present exemplary embodiment. In the present exemplary embodiment, the present invention is realized by an X-ray imaging system similar to that of the first exemplary embodiment. Therefore, a description of the configuration of the X-ray imaging system is omitted here. However, a program stored in the ROM 107 is used to execute processing illustrated in the flow chart of FIG. 6. A flow of processing executed by the X-ray imaging system is described with reference to the flow chart of FIG. 6. Processing in steps S601 through S603, S608, and S609, respectively, is similar to steps S301 through S303, S305, and S306 in the first exemplary embodiment, so that descriptions thereof are omitted here.

In step S604, the display control unit 207 displays the acquired moving image. The defective pixels are not necessarily displayed in step S604. In step S605, the display control unit 207 designates a region in the moving image according to an input by the user on the moving image. This designation is performed according to an input for selecting the region on the screen by using, for example, the mouse 110 of the input unit 209. Thus designated region is displayed on the screen. Then, the transmission instruction unit 208 issues an instruction to the detector 102 so as to transmit the defective pixel map. The anomalous pixel acquisition unit 206 acquires the defective pixel map within the designated region. In step S606, the display control unit 207 generates image data for displaying while differentiating a display format for the defective pixels of the designated region from a display format for the defective pixels within the regions other than the designated region and causes the display unit 103 to display the image data. Examples of the display format include a method for using different marks, a method for using different colors and a method for using different periods of blinks inside the designated region and outside the designated region, a method for not displaying the defective pixels outside the designated region and a method for highlighting the defective pixels only inside the designated region. Accordingly, the defective pixels of the region the user desires to pay an attention can be highlighted to be provided to the user and the attention of the user can be drawn to the defective pixels within the target region.

In step S607, when the user clicks a position adjustment button on the screen by using the mouse 110 of the input unit 209, the image processing apparatus 101 searches for the adjustment amount of the defective pixels within the designated region such that the number of defective pixels becomes less as much as possible, thereby providing the adjustment amount. Such a method is considered in searching for the adjustment amount that, for example, a threshold limit value of the adjustment amount is preliminary calculated and all of the defective pixels are adjusted within a range of the threshold limit value in order to find out the adjustment amount capable of obtaining the minimum value of the defective pixel. Based on the adjustment amount as provided above, the position adjustment is performed. The position adjustment is performed by, for example, physically moving the detector 102 or the object (not shown). In a case where the detector 102 is moved, the position adjustment is performed such that a moving unit of the detector 102 is provided on a table where the detector 102 is disposed and thereafter the detector 102 is moved for a necessary distance. This is described in detail below. Alternatively, in a case where the object is moved, the position adjustment is performed such that a table on which the object is placed is automatically moved for a predetermined amount. Alternatively, the user may manually move the tables without using the auto adjustment unit.

FIGS. 7A through 7C illustrate examples of display of a screen and an example of a schematic position adjustment. The display screen illustrated in FIG. 7A displays a moving image and a region designated according to an input by the user in the displayed moving image. The defective pixels included in the region are indicated in black color and the defective pixels included in the other regions are indicated in white color. Since the drawings cannot be colored, the defective pixels are indicated in black color or white color. However, more easy confirmation can be achieved by actually coloring the defective pixels. According to the above, since the defective pixels included in the designated region is differently displayed from the defective pixels of the regions other than the designated region, an attention of the user can be drawn to the defective pixels of the target region.

On a screen illustrated in FIG. 7A, the searched adjustment amount is indicated. According to the displayed screen, the image is to be moved by 3 units rightward and by 1 unit downward. FIG. 7B illustrates the adjustment amount. When the user clicks the position adjustment button on the screen, the image processing apparatus 101 searches for and determines the adjustment amount. In a case where the determined adjustment amount indicates a movement of the image by 3 pixels rightward and 1 pixel downward, the position of the detector 102 is moved by using a table (not shown). A screen after the detector 102 is moved is illustrated in FIG. 7C. In FIG. 7C, no defective pixel of the region designated on the screen is indicated. With the above-described adjustment, a still image with less adverse effect of the defective pixels can be acquired.

In the above description, the defective pixels are exemplified as the anomalous pixels and an application example of the defective pixels is described. However, the application example of the present invention is not limited to the above. The other anomalous pixels such as a noise extracted according to a similar extraction method may also be exemplified.

In the above-described exemplary embodiment, a portion of a functional block executed through the program may be installed as an image processing board for the sake of a dedicated use.

In the above-described exemplary embodiment, the detector 102 is configured to include the extraction unit 203 for extracting the anomalous pixels and the correction unit 204 for correcting the anomalous pixels. However, the exemplary embodiment of the present invention is not limited to the above-described configuration. Namely, an extraction unit and a correction unit may be included in the image processing apparatus 101.

A program which realizes the functions of the above-described exemplary embodiment may be supplied to an information processing apparatus or a system via a network or a storage medium. In this case, an apparatus or a system, which stores the supplied program, reads the program, and then executes the program, the program itself, or the storage medium itself are also included in the present invention.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-214696 filed Sep. 16, 2009, which is hereby incorporated by reference herein in its entirety.

What is claimed is:

1. An image processing apparatus comprising:
an image acquisition unit configured to acquire an image captured according to a specific image capturing method;
an anomalous pixel acquisition unit configured to acquire a position of at least one anomalous pixel occurring according to an image capturing method different from said specific image capturing method;
a designation unit configured to designate a region in the captured image;
a presenting unit configured to present an adjustment amount for adjusting a position of an imaging apparatus according to the anomalous pixel included in the designated region; and
a display control unit configured to cause a display unit to display the position of the acquired anomalous pixel together with the captured image according to the specific image capturing method,
wherein when the imaging apparatus is adjusted according to the adjustment amount, the at least one anomalous pixel is removed from the designated region.

2. The image processing apparatus according to claim 1, wherein the display control unit causes the position of the acquired anomalous pixel to be displayed in superimposition on the captured image.

3. The image processing apparatus according to claim 2, wherein the display control unit changes a display format for the position of the anomalous pixel according to the designated region.

4. The image processing apparatus according to claim 1, wherein the specific image capturing method includes an image capturing method for capturing a moving image, and the image capturing method different from the specific image capturing method includes an image capturing method for capturing a still image.

5. The image processing apparatus according to claim 1, wherein the image acquisition unit acquires an image captured by an imaging apparatus that supports the specific image capturing method and the image capturing method different from the specific image capturing method.

6. An image processing method comprising:
acquiring an image captured according to a specific image capturing method;
acquiring a position of an anomalous pixel occurring on an image captured according to an image capturing method different from the specific image capturing method;
designating a region in the captured image;
presenting an adjustment amount for adjusting a position of an imaging apparatus according to the anomalous pixel included in the designated region; and
causing the acquired position of the anomalous pixel to be displayed together with the captured image according to the specific image capturing method,
wherein when the imaging apparatus is adjusted according to the adjustment amount, the at least one anomalous pixel is removed from the designated region.

7. A non-transitory computer-readable storage medium storing a program for causing a computer to execute a method comprising:
acquiring an image captured according to a specific image capturing method;
acquiring a position of an anomalous pixel occurring on an image captured according to an image capturing method different from the specific image capturing method;
designating a region in the captured image;
presenting an adjustment amount for adjusting a position of an imaging apparatus according to the anomalous pixel included in the designated region; and
causing the acquired position of the anomalous pixel to be displayed together with the captured image according to the specific image capturing method,
wherein when the imaging apparatus is adjusted according to the adjustment amount, the at least one anomalous pixel is removed from the designated region.

8. An image processing system comprising:
an imaging unit configured to support a plurality of image capturing methods for capturing an image;
an acquisition unit configured to acquire an image captured according to one image capturing method of the plurality of image capturing methods;
an extraction unit configured to extract a position of an anomalous pixel occurring on an image captured according to an image capturing method different from the one image capturing method of the plurality of image capturing methods;
a designation unit configured to designate a region in the captured image;
a presenting unit configured to present an adjustment amount for adjusting a position of an imaging apparatus according to the anomalous pixel included in the designated region; and
a display unit configured to display the extracted position of the anomalous pixel together with the captured image according to the specific image capturing method,
wherein when the imaging apparatus is adjusted according to the adjustment amount, the at least one anomalous pixel is removed from the designated region.

* * * * *